(12) United States Patent
Fiorini et al.

(10) Patent No.: US 11,543,839 B2
(45) Date of Patent: Jan. 3, 2023

(54) METHOD FOR MAINTAINING AN EQUILIBRIUM OF A PHYSICO-CHEMICAL PARAMETER OF A MEDIUM, ASSOCIATED COMPUTER PROGRAM PRODUCT AND ELECTRONIC MODULE

(71) Applicant: ONDILO, Saint-Cannat (FR)

(72) Inventors: Nicolas Fiorini, Pelissanne (FR); Didier Roussel, Pelissanne (FR)

(73) Assignee: ONDILO, Saint-Cannat (FR)

( * ) Notice: Subject to any disclaimer, the term of this patent is extended or adjusted under 35 U.S.C. 154(b) by 418 days.

(21) Appl. No.: 16/471,382

(22) PCT Filed: Dec. 20, 2017

(86) PCT No.: PCT/FR2017/053747
§ 371 (c)(1),
(2) Date: Jun. 19, 2019

(87) PCT Pub. No.: WO2018/115751
PCT Pub. Date: Jun. 28, 2018

(65) Prior Publication Data
US 2019/0332131 A1    Oct. 31, 2019

(30) Foreign Application Priority Data

Dec. 20, 2016 (FR) .................................. 1662813

(51) Int. Cl.
*G05D 21/02* (2006.01)
*G01N 33/18* (2006.01)
*G05B 19/4155* (2006.01)

(52) U.S. Cl.
CPC ............. *G05D 21/02* (2013.01); *G01N 33/18* (2013.01); *G05B 19/4155* (2013.01); *G05B 2219/40585* (2013.01)

(58) Field of Classification Search
CPC ...... G05B 2219/40585; G05B 19/4155; G16Z 99/00; G01N 23/18; G01N 33/18; G05D 21/02
See application file for complete search history.

(56) References Cited

U.S. PATENT DOCUMENTS

| 9,222,950 B2 * | 12/2015 | Satomura ................. G01N 1/28 |
| 2016/0026171 A1 * | 1/2016 | Dash ....................... G05B 13/04 700/267 |

FOREIGN PATENT DOCUMENTS

| EP | 2273039 A1 | 1/2011 |
| FR | 2969281 A1 | 6/2012 |

(Continued)

OTHER PUBLICATIONS

International Search Report (PCT/ISA/210) dated Feb. 8, 2018, by the European Patent Office as the International Searching Authority for International Application No. PCT/FR2017/053747.

(Continued)

*Primary Examiner* — Shogo Sasaki
(74) *Attorney, Agent, or Firm* — Buchanan Ingersoll & Rooney PC (57) ABSTRACT

The invention relates to a method for maintaining an equilibrium of a physico-chemical parameter of a medium, and for recovering the equilibrium in case of loss of the latter. More precisely the method makes it possible to estimate the relevance of a corrective action on the medium in order to recover an equilibrium. The method is implemented by the processing unit of a system for regulating the medium. The invention applies in a non-limiting manner to the regulation of the equilibrium of the bathing water of a swimming pool.

17 Claims, 2 Drawing Sheets

(56) References Cited

FOREIGN PATENT DOCUMENTS

| FR | 2981474 A1 | 4/2013 |
|----|------------|--------|
| WO | 2004029625 A2 | 4/2004 |
| WO | 2010052419 A1 | 5/2010 |
| WO | 2015033032 A1 | 3/2015 |
| WO | 2015082863 A1 | 6/2015 |
| WO | 2016151232 A1 | 9/2016 |

OTHER PUBLICATIONS

Written Opinion (PCT/ISA/237) dated Feb. 8, 2018, by the European Patent Office as the International Searching Authority for International Application No. PCT/FR2017/053747.

Hector Ricardo Hernandez De Leon, "Supervision et diagnostic des procedes de production d'eau potable", Sep. 27, 2006, pp. 65-80, retrieved from the internet: https://tel.archives-ouvertes.fr/tel-00136157/document.

* cited by examiner

METHOD FOR MAINTAINING AN EQUILIBRIUM OF A PHYSICO-CHEMICAL PARAMETER OF A MEDIUM, ASSOCIATED COMPUTER PROGRAM PRODUCT AND ELECTRONIC MODULE

The invention relates to a method for maintaining an equilibrium of one or more physico-chemical parameters characterizing a medium and for recovering said equilibrium in case of a loss of the latter. More precisely, the invention relates to a method for making it possible to estimate the appropriateness of a corrective action on said medium for the purpose of recovering an equilibrium. As an advantageous but nonlimiting example, such a corrective action can consist, for example, of an addition of a chemical agent, of which the dosage is adjusted to the medium in consideration, thus preventing any overconsumption which is unnecessary or harmful for said medium.

The invention will be described in a preferred but nonlimiting manner by means of an application example pertaining to the maintenance of the equilibrium of the bathing water of a swimming pool. However, the invention cannot be limited to such a medium, the latter possibly consisting of a cultivation space of a garden, topsoil, etc.

In order to ensure healthy bathing and year-round operation of the equipment of a swimming pool, the bathing water of the swimming pool must meet several criteria relating to the disinfection of the water and the equilibrium of the latter. In fact, the water of a swimming pool is by definition impure, that is to say, in addition to the water molecules, it consists of several chemical elements such as, as nonlimiting examples, calcium, magnesium, sodium, etc. Thus, in some cases, the uncontrolled quantity of such chemical elements within the water of a swimming pool can disturb the equilibrium of said swimming pool water. As a nonlimiting example, an increase in the calcium proportion can disrupt the equilibrium of such a composition and result in a calcium carbonate deposit on swimming pool equipment such as, for example, pipes and/or coating of the basin, etc. Such a calcium carbonate deposit can then damage said equipment and cause turbidity of the water. Moreover, in general, the water of a swimming pool is also territory for microorganisms of varying degrees of harmfulness for a bather. As nonlimiting examples, such microorganisms can consist of algae, bacteria, fungi, etc. Said microorganisms primarily feed on organic detritus contributed by the outside environment, such as, for example, dust, pollen, insects, etc., or introduced by the bathers, such as, for example, detritus or elements conveyed by sweat, skin, cosmetic products, etc. Due to the presence of numerous microorganisms within the water of the swimming pool, said microorganisms proliferate, thus also resulting in a microbiological imbalance. Such an imbalance can be reflected, for example, in uncontrolled proliferation of algae in the swimming pool. A deposit of algae can then appear on the walls of said swimming pool, and the water can take on a green hue, which is not inviting even to hardy bathers.

In order to sanitize the water and recover an equilibrium, several corrective actions can thus be implemented. As a nonlimiting example, a first action can consist in filtering the water to remove solid detritus contributed by the outside environment and the bathers from the medium, by means of, for example, the manual use of a net or by the automatic operation of an automated filtration device, also known as "skimmer". Although this type of action makes it possible to remove all or part of the solid detritus present within the water of a swimming pool, it does not make it possible to eliminate the microorganisms, the latter being generally too small to be retained in such filters, and thus to properly disinfect the water. In order to properly disinfect the water, that is to say to eliminate the microorganisms, it is necessary to use, as a variant or additionally, chemical products or agents such as, for example, chlorine and/or algicides. Such chemical products can be introduced manually or automatically.

The equilibrium of a swimming pool can be estimated and regulated based on several physical variables such as, for example, as a nonlimiting example, the hydrogen potential commonly referred to as the "pH." The latter makes it possible to establish the acidity or the alkalinity of a medium, that is to say whether the medium is alkaline, neutral or acidic. As a nonlimiting example, the water of a swimming pool ideally has a pH between 6.9 and 7.6. Such a pH measurement makes it possible to:

reinforce the effectiveness of the disinfecting agents, such as, for example, chlorine;
decrease irritation of the skin and eyes of the bathers;
avoid corrosion of the metal equipment used in connection with the medium;
limit the precipitation of calcium salts within the water of a swimming pool, such as calcium salts that that can cause scaling of the swimming pool equipment, etc.

The pH measurement can vary as a function of the type of disinfectant used, the temperature of the water, of the rain, the occupancy load of the basin, etc. The ideal pH of the water of a swimming pool moreover can depend on the type of coating of said swimming pool. In order to regulate the value of the pH measurement, it is possible to introduce chemical products or agents which make it possible to decrease or increase the value of said pH measurement, so as to finally reach a value between 6.9 and 7.6.

The equilibrium of a swimming pool can moreover be estimated on the basis of the value of a parameter referred to as "CAT," an acronym for Complete Alkalimetric Titer, reflecting the alkalinity of the water, that is to say the concentration of carbonate and hydrogen carbonate ions in the water, or on the basis of the value of a parameter referred to as "HT," an acronym for Hydrotimetric Titer, reflecting the hardness of the water, that is to say the calcium and magnesium concentration of the water, indicating the mineralization of the water. Ideally, the value of the CAT is between eighty (80) and one hundred and twenty (120) milligrams per liter, and the value of the HT is between a hundred (100) and two hundred and fifty (250) milligrams per liter. The values of the CAT and/or of the pH directly influence the value of the pH or the physico-chemical properties of the water of a basin. Thus, when the value of the CAT is too low, the pH becomes unstable, that is to say it can vary rapidly from an alkaline state to an acidic state without being able to stabilize correctly in one of these states. As to the HT, when it is too low, it can cause irritation of the bathers' eyes and skin. In contrast, when the respective CAT and/or HT values are too high, the water can become turbid and a scale or calcium carbonate deposit can be observed on the walls and in the pipes of the water filtration or heating equipment of the swimming pool, for example.

The disinfecting power for a swimming pool, that is to say the quantity of active disinfecting chemical agent(s) in the water of said swimming pool, can be determined based on the value of the oxidation-reduction potential, also referred to as the oxidation-reduction potential, of said water, which is generally expressed in millivolts. Such a potential makes it possible to determine the oxidizing potential of a disinfecting chemical agent, thus making it possible to predict the reactivity of said disinfecting chemical agent. As nonlimiting examples, a high redox potential can mean a high concentration of disinfecting chemical agent in the bathing water, while a low redox potential can mean a low concentration of disinfecting chemical agent. Also, as nonlimiting examples, swimming pool water can be considered to be disinfected if the redox potential is greater than or equal to six hundred and fifty (650) millivolts. Moreover, the oxidation of the disinfecting chemical agents and thus their disinfecting power can depend on the current value of the pH and current value of the CAT in the medium.

The equilibrium of a swimming pool can therefore be estimated based on several physico-chemical parameters, variables and/or measurements, such physico-chemical parameters, variables and/or measurements influencing one another, as described above.

In order to maintain the equilibrium of the water of one's swimming pool, an owner, a bather or in general an operator can periodically check various physico-chemical parameters of said swimming pool, for example, once daily by means of parameter testers or more generally by means of an analysis kit making it possible to estimate in particular the chlorine content of the swimming pool, the value of the pH and the value of the CAT. Such analysis kits can be in the form of strips dedicated to a specific physico-chemical parameter, said strips having to be inserted in the water of the swimming pool. Such a strip can be dedicated, for example, to estimating the pH. In contact with the water, said strip turns color by chemical reaction between the said strip and the water of the swimming pool. The strip thus colored can then be compared to a predetermined color table as a function of predefined typical pH levels. The owner or the user of a swimming pool can thus estimate the pH value of his/her swimming pool. Although enabling the rapid and easy determination of the current value of the pH of the water of a swimming pool, the use of such strips nevertheless has several disadvantages such as, for example, a lack of precision since the color table is generally limited, and a limited useful life over time since the strips expire after a certain time.

As a variant, another method can consist in using an electronic tester or a probe, for example, a pH probe or an oxidation-reduction potential probe. The current value of the measurement delivered by such an electronic tester or such a probe can thus be displayed by said electronic tester. However, although very practical, such electronic testers have to be calibrated based on buffer solutions. Numerous errors can thus occur in case of a poor calibration of said testers or probes, resulting in an incorrect interpretation of the value of the pH when taking measurements and possibly then generating one or more inappropriate corrective actions.

Once the current value of a physico-chemical parameter of a swimming pool is known, such as, for example, the value of the pH, a user, an owner or an operator of the swimming pool can manually add a determined chemical agent making it possible to reestablish the equilibrium of the swimming pool. For example, if the measured value of the pH is greater than 7.6, the water of the swimming pool is considered to be too alkaline. Therefore, it is necessary to add to said water a chemical agent making it possible to lower said pH and bring the water of the swimming pool to neutral, that is to say, bring it to a pH value close to or approximately equal to 7, or to a pH value between 6.9 and 7.6. On the other hand, if the value of the pH is less than 6.9, the water of the swimming pool is acidic. In that case, a chemical agent has to be added to said water, making it possible to increase said pH and to bring the water of the swimming pool to neutral.

As a variant, according to a second method, the management of the concentration of one or more disinfecting chemical agents or more generally of the measurements of the respective values of one or more physico-chemical parameters of a swimming pool can be carried out by one or more automated devices measuring current values of said parameters and automatically introducing the or said chemical agent(s) depending on a distance measured between the nominal value of a given physico-chemical parameter with regard to the measured value.

However, the strips or the automated devices described above have several disadvantages. In fact, said strips or said automated devices are generally specialized means for measuring a single physico-chemical parameter. Thus, in order to measure all or some of the parameters influencing the equilibrium of a swimming pool, it is necessary to invest in numerous measurement devices or means. In addition, the use of such strips or of such automated devices does not take into account certain interactions between parameters. For example, an excessively acidic pH can reduce the effectiveness of a disinfecting chemical agent, resulting in a risk of overdosage of the disinfecting chemical agent, whereas it might have been sufficient to instead increase the concentration of a pH amplifying chemical agent. In addition, during a manual introduction of one or more chemical agents in the medium in consideration, an operator generally must himself calculate the quantity of chemical agent to be introduced. In the case of a swimming pool, this quantity can depend on the size of the basin, the concentration of the chemical agent, etc. For a swimming pool of a private individual, an owner may often be baffled or unable to carry out the appropriate calculation. Thus, during said quantity calculation, new errors can occur, which can, after the introduction of said agent, disrupt the equilibrium of the swimming pool and, for example, affect the swimming pool equipment due to an excessively high chlorine level, for example.

The usual methods presented above make it possible to regulate certain physico-chemical parameters of the water of a swimming pool at a given time, without taking into consideration all the parameters of the swimming pool. A swimming pool can thus be saturated with chemical agent without anyone being aware of it. The addition of a chemical agent can thus turn out to be without effect, with the owner seeking to correct a parameter by disproportionate and ineffective introduction of a chemical agent.

The invention makes it possible to respond to all or some of the disadvantages raised by the known solutions by proposing an innovative method for maintaining the equilibrium of a medium such as a swimming pool.

Such a method procures numerous advantages, among which we can mention that it enables:
  consideration of a plurality of physico-chemical parameters of a medium;
  automatic and dynamic adaptation of corrective actions to the behaviors of a medium in particular;
  anticipation of the impact of certain factors, such as overvisitation or inclement weather, on the equilibrium of the medium, thus minimizing certain corrective actions if the latter were merely reactive;
  adaptation of said actions with regard to the environment of the medium, for example, with regard to exposure or vegetation of the surroundings;

support for the user during a manual addition of one or more chemical agents;

management of optimized resources by the use of the system in accordance with a client server environment;

long-lasting use of the equipment of the medium.

For this purpose, in particular, a method for maintaining an equilibrium of a physico-chemical parameter of a medium is provided, said method being implemented by a processing unit of a system for regulating said medium, said processing unit cooperating with storage means recording the data relating to a medium parameter. The storage means consequently comprise a first recording dedicated to said medium parameter and configured to store a current value of said parameter and a nominal value. In order to regulate such a system, said method comprises:

a step for reading the current value of said parameter;

a step for reading the nominal value of said parameter;

a step for estimating a distance between said nominal value and the current value;

a step for triggering an action depending on the value of said distance.

In order to maintain the equilibrium of a physico-chemical parameter of said medium, the recording dedicated to said medium parameter comprises a field for storing a time limit value for recovering a determined nominal value, and said method comprises:

before the step for triggering an action, a step for reading the value of the field for storing a time limit value;

the step for triggering an action depending on said distance being implemented if and only if the value of the field for storing a time limit value consists of a predetermined value characterizing the absence of definition of a time limit for recovering a determined nominal value.

Preferably, but in a nonlimiting manner, a method for maintaining an equilibrium of a physico-chemical parameter of a medium according to the invention, before the step for triggering an action, can comprise a step for elaborating said action depending on the value of said distance.

According to an advantageous but nonlimiting embodiment, the step for elaborating an action of said method can comprise a step for estimating a nominal value of said parameter.

As a variant or additionally, the step for elaborating an action of said method can comprise a step for defining a time limit value for recovering a determined nominal value depending on said action.

In addition, the step for triggering an action of a method for maintaining an equilibrium of a physico-chemical parameter of a medium according to the invention can consist in updating the recording dedicated to said parameter in order to register in it the nominal value of said parameter or the time limit value for recovering a determined nominal value depending on said action.

For implementing a determined action by the processing unit of the regulation system, the latter can cooperate with an actuator. The step for triggering an action of a method according to the invention can then consist in elaborating a command intended for said actuator in order to implement the action depending on the estimated distance.

In order to inform a user of a regulation system according to the invention about an action to be implemented, the processing unit can moreover cooperate with a human-machine rendering interface. The step for triggering an action of a method according to the invention can then consist in elaborating an instruction intended for said user and in triggering the rendering of said instruction by the human-machine rendering interface.

In order to transmit the effects of an associated action to all or some of the parameters of the system, the storage means can comprise a second recording dedicated to a second medium parameter and configured to store a nominal value and a current value of said second parameter. The process for maintaining an equilibrium of a physico-chemical parameter of a medium, after the step for elaborating an action, can then comprise a step for estimating a nominal value and a current value of said second parameter depending on the previously elaborated action.

To acknowledge a time limit of action, a method according to the invention can also comprise a step consisting in registering, in the field for storing a time limit value, a predetermined value characterizing the absence of a time limit definition, said step being implemented if the value of the distance between said nominal value and the current value confirms a distance that is substantially zero.

When an action does not have the expected effect, a method for maintaining an equilibrium of a physico-chemical parameter of a medium according to the invention can comprise a step for correcting an action before the step of triggering an action, said correction step being implemented if and only if:

the completion limit for recovering a nominal value has been reached;

the value of the distance between said nominal value and the current value is not zero.

According to an advantageous but nonlimiting embodiment example, the step for correcting an action of said method can comprise a step for estimating a new nominal value of said parameter.

Preferably but in a nonlimiting manner, the step for correcting an action of said method can moreover comprise a step for defining a time limit value for recovering a determined nominal value depending on said correction of an action.

Moreover, as a variant or additionally, the means for storing a regulation system can moreover comprise a current value of a preceding period. In order to limit or avoid an excessively high reactivity or variability of a parameter, the step for reading the current value of a method for maintaining an equilibrium of a physico-chemical parameter of a medium according to the invention can then consist in reading the preceding value and calculating a new current value based on said read values.

In order to anticipate a disturbing event that can alter an equilibrium, the storage means can also comprise anticipation data. The step for reading the current value of the method can then moreover consist in reading the anticipation data and calculating a new current value of the parameter based on said prediction value.

In order to determine the current value of a parameter, the processing unit can also cooperate with sensing means. Said method can thus comprise, before the step for reading the current value of said parameter, a step for triggering the acquisition of said value by said sensing means and registering said value as current value.

According to a second subject matter, the invention relates to a computer program product comprising one or more program instructions which can be run by a processing unit of an electronics module, said processing unit cooperating with sensing means and storage means, which, when they are executed or interpreted by said processing unit, trigger the implementation of a method for maintaining an equilibrium of a physico-chemical parameter of a medium according to the invention.

According to a third object, the invention relates to an electronic module comprising a processing unit cooperating with sensing means and storage means. Advantageously but in a nonlimiting manner, in order to carry out a method for maintaining an equilibrium of a physico-chemical parameter of a medium, said electronic module comprises instructions of a computer program product according to the invention in said storage means.

Other features and advantages will become clearer upon reading the following description referring to an embodiment example given for information and in a nonlimiting manner, and upon examination of the figures which accompany said embodiment example, among which.

As a preferred but nonlimiting application example, the invention will be described by means of an application pertaining to maintaining an equilibrium of one or more parameters of the bathing water W of a swimming pool SWP. Such an application is described in particular by means of a regulation system according to the invention in reference to FIG. 1. Such a regulation system according to the invention includes sensing means SenM, inserted in the bathing water W of said swimming pool SWP. An automated chemical agent distribution device 14 of said regulation system is then connected to the basin of said swimming pool SWP by one or more pipes Pi, making it possible to release one or more chemical agents such as chlorine, for example, in said swimming pool. For this purpose, such an automated device 14 can cooperate with one or more reservoirs of chemical agents pH−, pH+, Cl−, Cl+. Said regulation system then comprises a processing unit PU cooperating with a human-machine instruction and rendering interface 15. Said processing unit PU moreover cooperates with said sensing means SenM and said automated device 14. The latter can be directly connected by a wired bus to said processing unit PU or, as a variant, they can be remote from said unit PU and cooperate via wireless connection, for example, by means of a network R1 or R3 of the Internet, Intranet, Bluetooth or WiFi type. The processing unit PU can moreover cooperate with a remote server S, via a wireless connection R2 of the Internet type, for example.

Figure 1:
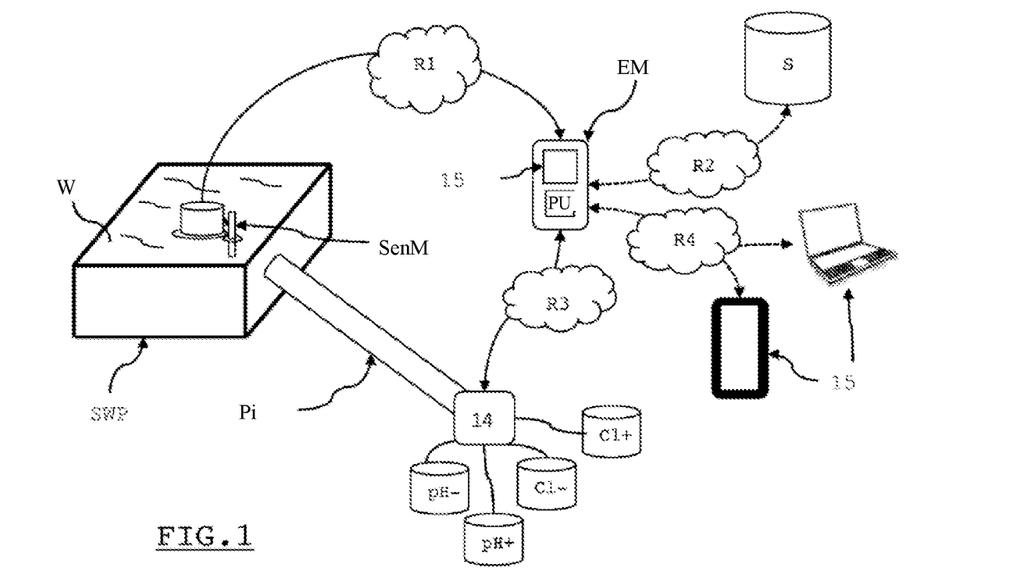
FIG. 1 describes a preferred but nonlimiting example of a system for regulating physico-chemical parameters of bathing water of a swimming pool.

According to an advantageous but nonlimiting embodiment variant of the invention described in reference to FIG. 1, the human-machine interface 15 and the processing unit PU of said regulation system can cooperate within the same electronics equipment EM. As a variant, the human-machine interface 15 and the processing unit PU can be separate. For example, the human-machine interface 15 can be the interface of a third-party electronics device such as a mobile telephone or a microcomputer; said interface 15 and said processing unit PU then communicate via a wireless connection R4, for example, Bluetooth, WiFi or Ethernet.

As a variant or additionally, the automated distribution device 14 can be supplemented by a human action for the purpose, for example, of manually actuating a filter or introducing a chlorine pellet in the bathing water of the swimming pool. When the distribution of chemical agents is carried out manually, a user of the regulation system can thus become aware of the action to be carried out by means of an instruction rendered by the human-machine rendering interface 15. Said instruction can be elaborated beforehand by the processing unit PU. Once the action is implemented, the user can then enter, by means of a human-machine interface 15, an instruction for the purpose of acknowledging said action, said instruction being processed by the processing unit PU.

Figure 2:
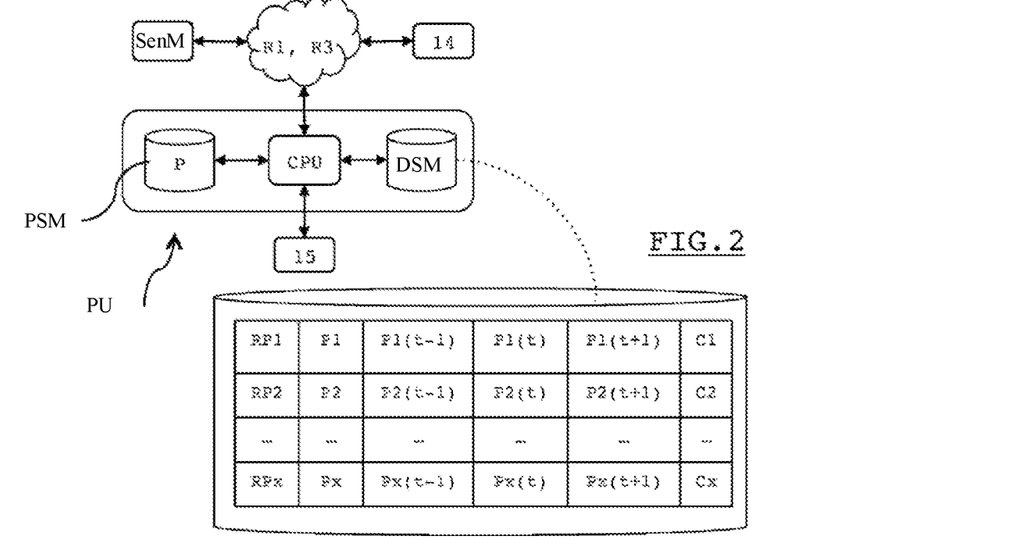
FIG. 2 describes a functional diagram of a system for regulating a medium, comprising a sensing means, storage means and a processing unit for implementing a method for maintaining in equilibrium the physico-chemical parameters of said medium according to the invention.

FIG. 2 presents the structural architecture of a system 10 for regulating a swimming pool according to the invention. In order to maintain one or more physico-chemical parameters of said swimming pool in equilibrium, a regulation system according to the invention comprises a processing unit PU, included, for example, within an electronic module EM available to the person in charge of maintaining the swimming pool, as described in reference to FIG. 1. Such an electronic module EM can consist of a dedicated device or can consist of a personal computer or a mobile telephone or any other electronic equipment. Such a processing unit PU advantageously comprises a microcontroller CPU cooperating, by coupling and/or by wired bus, with data storage means DSM and/or program storage means PSM. Such storage means consist essentially of one or more nonvolatile memories. The program storage means PSM are advantageously configured to record in particular instructions of a program P, which, when executed or interpreted by said microcontroller CPU, trigger the implementation of a method for maintaining in an equilibrium of one or more physico-chemical parameters of a medium according to the invention. As to the data storage means DSM, they are configured in particular to record data structures necessary for implementing a method according to the invention. As nonlimiting examples, said data can be recorded in tables including one or more recordings or chained data structures.

As a variant or additionally, still according to a nonlimiting embodiment of a regulation system according to the invention, the latter can comprise one or more sensing means SenM cooperating with the processing unit PU. The latter is then tasked with collecting the data supplied by said sensing means SenM. The sensing means SenM can measure one or more physico-chemical parameters associated with a medium such as, as nonlimiting examples, the pH, the CAT, the HT, the oxidation-reduction potential and/or the temperature. As indicated in FIGS. 1 and 2, the sensing means SenM then produce a value, hereafter referred to as current value Px(t), of the parameter Px considered at each determined time unit t. The current value Px(t) is then recorded in the data storage means DSM. According to a nonlimiting embodiment variant, the recording of time data t characterizing the current period can be carried out jointly with the recording of the current value Px(t). As nonlimiting examples, the sensing means SenM can consist of a pH probe or an oxidation-reduction probe, dedicated respectively to the measurement of the current value of the pH and of the oxidizing potential of the water W of the swimming pool SWP.

As a variant or additionally, the processing unit PU can moreover cooperate with an actuator 14, making it possible to deliver a given quantity of chemical agent into the medium W. According to FIG. 1, as nonlimiting examples, such an actuator 14 can consist of one or more automatic distributors of chlorine Cl−, Cl+ and/or of alkaline chemical agents pH+ or acidic chemical agents pH− and, for example, it can be directly connected by a wired bus to said processing unit PU or, as a variant, it can be remote from said processing unit PU and cooperate via a wireless connection, for example, by means of a network R1, R3 of the Internet, Intranet, Bluetooth, WiFi type, or any other equivalent protocol.

As a variant or additionally, the processing unit PU can moreover cooperate with a human-machine instruction and/or rendering interface 15. Said interface 15 enables a user of the system to receive recommendations of corrective actions elaborated by the processing unit PU and to transmit, for example, a message of acknowledgment of completion of such an action, if said action requires a manual intervention, as described above with regard to FIG. 1. Such an instruction and rendering interface 15 can consist, for example, of a touch screen or be in the form of any other instruction and rendering means making it possible for a user to interact with said regulation system. As a variant, a regulation system according to the invention can cooperate with two different human-machine interfaces 15 for translating actions originating from a user and rendering graphic and/or sound content in a separate manner for said user. Such an instruction interface can consist, for example, of a keyboard, a microphone, a mouse or any other pointing device. As for such a rendering device, it can consist, for example, of a screen or a loudspeaker.

In order to facilitate the understanding of the invention, the storage means PSM and DSM are represented in FIG. 2 as different functional elements. The storage means DSM and PSM could also and optionally constitute only one and the same physical resource. In the same manner, the processing unit PU could be a processing unit of one or more communicating electronic devices cooperating with the storage means DSM and PSM. The invention can then be adapted to a computerised environment of the client-server type, that is to say that client electronic devices, such as a unit for collecting data originating from sensing means SenM, can be connected by means of a communication network R2 to a server S implementing a method for maintaining an equilibrium of one or more physico-chemical parameters of a medium according to the invention. Thus, the electronic devices can access the functionalities offered by said server S, while maintaining the costs of implementation.

In a preferred but nonlimiting example of the invention, data can be recorded in one or more data structures, each comprising one or more recordings, within data storage means DSM. As a nonlimiting example, said recordings can be dedicated to or associated with one or more medium parameters and/or one or more corrective actions, respectively. As a variant, the different data structures mentioned above can constitute only one logical entity or can be according to any other representation mode and cannot constitute a limitation for the invention.

The data structure comprising recordings dedicated to one or more medium parameters can thus comprise recordings RP1 ... RPx associated with medium parameters P1 ... Px, respectively. The recordings can be grouped in the form of an ordered table of x recordings. Thus, the first recording of the table comprises data pertaining to a first parameter P1, the second element of the table comprises data pertaining to a second parameter P2, and so on, until the parameter Px recording the data pertaining to a parameter of rank x is reached. For the sake of simplicity, we will use "Px" as name for any one of the medium parameters P1, P2, Px and "RPx" for the recording associated with it.

Each recording RPx associated with a physico-chemical parameter Px of a medium W can be configured to store data necessary for and pertaining to the maintenance of the equilibrium of said parameter Px. Said data associated with a determined physico-chemical parameter Px can then be relative to a current period t and correspond, as examples, to an identifier of parameter Px, a current value Px (t) of said parameter Px measured or calculated by the sensing means SenM or by the processing unit PU respectively, a value Px (t−n) acquired and stored during a preceding period t−n, an estimated nominal value Px (t+n) of the parameter Px for a subsequent period t+n, n being a whole number greater than or equal to 1, a time limit value Cx for recovering such a nominal value Px (t+n) of a parameter and optionally the value of a distance Δ between said nominal value Px (t+n) and the current value Px (t). In the sense of the invention and in the entire document, "nominal value" is understood to mean a target or expected value describing a normal state of the medium. For example, in the context of a swimming pool, the nominal value of the parameter pH of the water can be fixed at 6.8. Additionally, such a recording can store a value characterizing the timestamp of the current period t and anticipation data AD. Such anticipation data AD can, as nonlimiting examples, consist of meteorological forecast data or of data characterizing the future use of the medium by humans or animals, etc.

In addition, such a recording RPx, associated with a physico-chemical parameter Px of a medium W, can be configured to store data necessary for the elaboration of an action with regard to a previously calculated distance Δ. Such a recording can comprise an action identifier, produced data characterizing, as nonlimiting examples, specifications pertaining to a dosage of a determined chemical agent, an attribute characterizing an execution priority, features of the medium such as, for example, the coating type of the basin of the swimming pool, etc. In this regard, the program storage means PSM can comprise a data base of different corrective actions, which is optionally adjusted by one or more parameters of execution of the action, whose respective default values can be stored in a table in the data storage means DSM.

Figure 3:
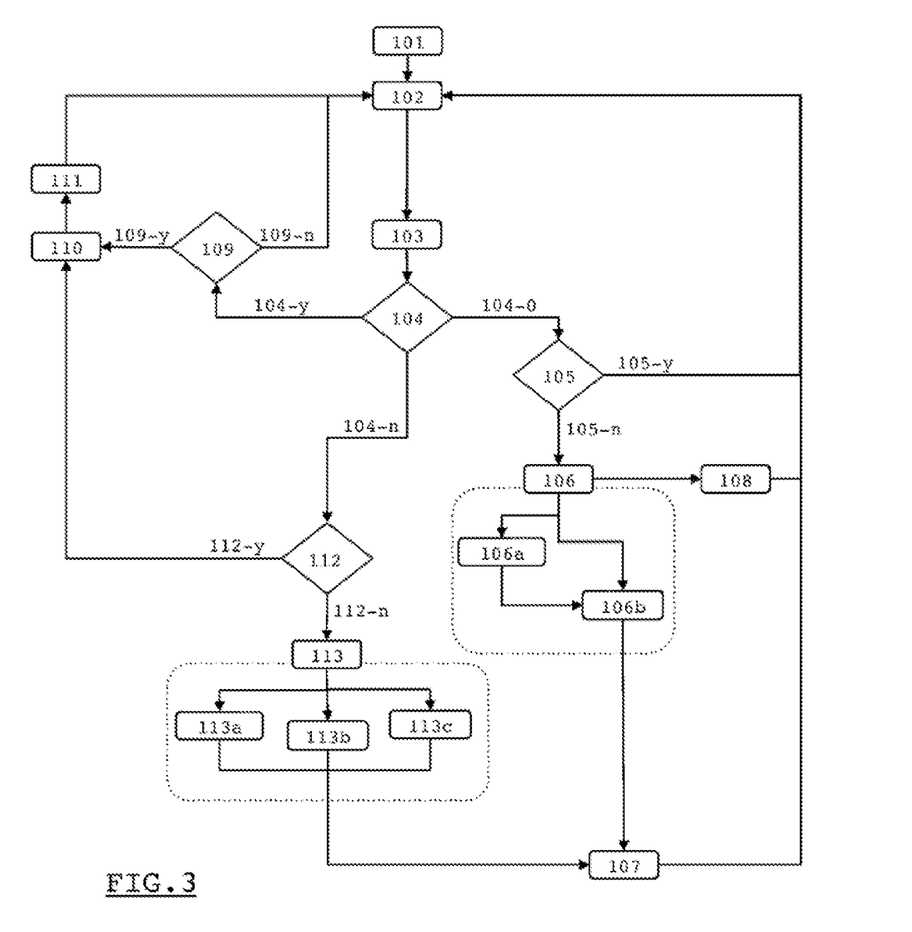
FIG. 3 describes a preferred but nonlimiting embodiment of a functional diagram of a method for maintaining such an equilibrium according to the invention.

Let us now describe, in reference to FIG. 3, a functional diagram of a method 100 for maintaining in equilibrium one or more physico-chemical parameters of a medium W according to the invention such as, for example, a swimming pool or the soil of a garden.

A method 100 for maintaining in equilibrium one or more physico-chemical parameters of medium W according to the invention can be implemented iteratively in accordance with a given period, such as, as nonlimiting examples, every six hours or every twenty-four hours or in accordance with any other predetermined period. As a variant or additionally, the implementation of the method 100 can be triggered in reaction to a triggering event such as, as nonlimiting examples, an updating of the data storage means DSM or a new registration in said data storage means DSM. According to another example of a triggering event, said method can be implemented after a request of a user of the regulation system, that is to say after the reception of an instruction message originating from the human-machine instruction interface 15 of said regulation system.

In addition, the method 100 can be implemented for maintaining or regulating a plurality of physico-chemical parameters of a medium W successively or together. Optionally, each physico-chemical parameter Px can have periodicity of regulation and/or follow-up identical to or different from the others. As a preferred but nonlimiting example, the method 100 implemented for maintaining or regulating the pH can be implemented once daily, while the method 100 implemented for regulating the Complete Alcalimetric Titer CAT can be triggered once weekly.

In reference to FIG. 3, a method 100 for maintaining a physico-chemical parameter of a medium W according to the invention, which is advantageously implemented by the processing unit PU of a system for regulating a medium, as described in reference to FIGS. 1 and 2, comprises a first step 102 and a second step 103 for respectively reading the current value Px (t) and the nominal value Px (t+n) of a recording RPx associated with a parameter Px within the data storage means DSM, such as, as an example, a recording dedicated to the regulation of the pH. As a nonlimiting example, such a nominal value Px (t+n) can consist of a determined value according to which the medium is balanced and healthy for correct use. As mentioned above, the pH of the water of a swimming pool can ideally be between 6.9 and 7.6. Outside this range of values, it can be necessary to regulate the value of the pH by introducing a chemical agent into the bathing water of said swimming pool, for example, an alkaline chemical agent if the pH is too acidic and an acidic chemical agent if the pH is too alkaline. Thus, the nominal value Px (t+n) can then be equal to any value between 6.9 and 7.6. As a variant or additionally, the recording RPx dedicated to or associated with a parameter Px of a medium can comprise a minimum nominal value, for example, for a recording dedicated to the pH, a minimum nominal value equal to 6.9, and a maximum nominal value, for example, for a recording dedicated to the pH, a minimum nominal value equal to 7.6. The step 103 then consists in reading said maximum nominal value and minimum nominal value. Finally, again as a variant or additionally, the nominal value Px (t+n) of a medium parameter Px can consist of an interval of values.

As we will see in the remainder of the document, the current value Px (t) of a parameter Px, read in the step 102, can advantageously be estimated or measured beforehand. When such a current value Px (t) is measured, the method 100 can comprise a step 101, before the step 102, for reading the current value Px (t), for triggering the acquisition of said value Px (t) by the sensing means SenM of a regulation system such as that described in reference to FIGS. 1 and 2 and registering said value as current value Px (t) within the data storage means DSM. When the method 100 is configured to maintain the pH of the water of a swimming pool, such sensing means SenM can consist of a pH probe making it possible to measure the current value Px (t) of the pH in the swimming pool water during the period t.

A method 100 for maintaining a physico-chemical parameter of a medium according to the invention then comprises a step 104 for reading the value contained in the field of the recording RPx dedicated to the medium parameter Px storing a possible time limit value Cx.

According to a first situation symbolized by the link 104-0 in FIG. 3, such a field can comprise a predetermined value characterizing an absence of definition of a time limit. Such a value can then consist, as a nonlimiting example, of an "empty" or "zero" value, known generally in computer language by the name of "VOID." When no time limit definition has been formulated, the method 100 then comprises a step 105 for estimating a distance Δ between the nominal value Px (t+n) and the current value Px (t). Such a distance Δ makes it possible to confirm a relative equality, situation which is symbolized by the link 105-y in FIG. 3, or, on the other hand, a clear difference between said nominal and current values, situation symbolized by the link 105-n in FIG. 3. If said distance confirms a relative equality, the current iteration of the method 100 is completed: the method will be implemented again in the next iteration.

As a nonlimiting example, when the studied parameter Px is the pH, the step 105 can consist in subtracting the current value Px (t), for example, the value 4.5, from the nominal value Px (t+n), for example, 7.3. If the result thus obtained is positive, the pH of the swimming pool can be considered to be too acidic. On the other hand, if the result is negative, the pH of the swimming pool can be considered to be too alkaline. Finally, when the result is equal to zero "0," the current value Px (t) and the nominal value Px (t+n) are substantially identical, that is to say, the pH of the swimming pool has reached or is equal to its nominal value or target value, the equilibrium of the pH within the swimming pool is thus maintained. As a variant or additionally, it is possible to determine a tolerance range, for example, +0.5 and −0.5, around the value of the distance Δ, wherein the current value Px (t) is substantially equal to the nominal value Px (t+n), for example, zero. If the result of said subtraction is within the tolerance range, during the step 105, the method 100 can consider the nominal value Px (t+n) and the current value Px (t) to be identical. On the other hand, if the value of the distance Δ is different from zero and/or said value of the distance Δ is not within a defined tolerance range, during the step 105, the method 100 can consider the nominal value Px (t+n) and the current value Px (t) to be different. As a variant or additionally, the step 105 of said method 100 can consist in comparing the current value Px (t) to the nominal value Px (t+n) of the physico-chemical parameter Px of interest according to known mathematical functions for determining a distance Δ between the current value Px (t) and the nominal value Px (t+n) of said parameter Px. As a nonlimiting example, the step 105 can consist in estimating the distance Δ in the form of a ratio of the current value Px (t) to the nominal value Px (t+n), for example, by dividing the current value Px (t) by the nominal value Px (t+n).

If the step 105 confirms a difference between the current value Px (t) and the nominal value Px (t+n), situation symbolized by the link 105-n in FIG. 3, then a method 100 for maintaining a parameter Px of a medium comprises a step 106 for elaborating a corrective action in order to attempt to recover a current value Px (t) close to the nominal value Px (t+n). Such a step 106 can consist in elaborating an action as a function of the distance Δ estimated beforehand. As a nonlimiting example, if the distance Δ reflects an excessively acidic pH, the step 106 can consist in elaborating an action seeking to increase the value of the pH, for example, by adding an alkaline chemical agent pH+. The quantity of chemical agent to be introduced into the medium, more particularly a swimming pool, is generally determined by the manufacturer of said chemical agent and depends on the volume of bathing water and the value of the pH in the swimming pool. In order to avoid an excessive addition of product, the step 106 can consist in extracting manufacturer data recorded beforehand in the data storage means DSM and calculating an appropriate quantity or dosage of chemical agent. The quantity of chemical agent to be introduced in the swimming pool can be weighted by the distance Δ between the current value Px (t) and the nominal value Px (t+n). As a variant or additionally, such a step 106 for elaborating a corrective action can moreover consist in estimating a filtration time of the bathing water W of the swimming pool SWP, as described in reference to FIG. 1, for a determined duration, for example, three hours.

According to a nonlimiting embodiment of a method for maintaining a physico-chemical parameter Px according to the invention, the step 106 can comprise a step 106a for estimating a nominal value Px (t+n) with regard to the elaborated action. For example, such a step 106a can consist in estimating the effect of an addition of a previously calculated quantity of chemical agent on the current value Px (t) of the medium parameter Px in consideration during a subsequent period t+n. Thus, if the current value Px (t) of the pH is equal to 4.2, the addition of a determined quantity of an alkaline chemical agent should cause the value of the pH to approach 6.9. The current value Px (t) should thus approach a nominal value Px (t+n) equal to 6.9.

According to another nonlimiting embodiment of a method for maintaining a physico-chemical parameter Px according to the invention, as a variant or additionally, the step 106 can comprise a step 106b for defining or estimating a time limit value Cx, that is to say, a date when or a duration after which the current value Px (t) and the nominal value Px (t+n) of the parameter Px should be substantially identical. A time limit value Cx can thus consist of a predetermined value characterizing the estimated duration or time period for the current value Px (t) of a parameter Px in consideration to recover a nominal value Px (t+n). When the parameter Px in consideration is the pH, after the addition of a chemical agent, it can be necessary to wait for one hour for the pH of the water of a swimming pool to stabilize. For this purpose, the time limit value Cx can be associated with an increasing or decreasing counter making it possible to count a determined number of time units, said counter being moved regularly at each time unit. Any other method or any other material element could be used for estimating or defining such a time limit value. Thus, as a variant or additionally, according to the invention, the time limit value Cx could consist of an absolute timestamp, that is to say a date and a time. For this purpose, the processing unit PU of a regulation system comprises or cooperates with an internal clock, thus making it possible to compare the current date and time with said time limit value.

A method 100 for maintaining a parameter Px of a medium comprises now a step 107 for triggering a corrective action. Such a step 107 can consist in updating the recording dedicated to the parameter Px whose current value was at the initiative of the elaboration of said action, for example, by registering in it the respective previously estimated time limit value Cx and normal value Px (t+n). When the processing unit PU of a regulation system as described in reference to FIG. 2 cooperates with an actuator 14, the step 107 can, as a variant or additionally, consist in elaborating a command intended for said actuator 14, said command comprising the nature and the quantity of chemical agent to be added to the water of the swimming pool. Also, said command can comprise an attribute characterizing the use of the actuator 14 cooperating with the processing unit PU.

According to another embodiment variant of a method 100 for maintaining a parameter Px of a medium according to the invention, when the processing unit PU cooperates with a human-machine rendering interface 15, the step 107 can consist in elaborating and transmitting an instruction in the form of a message intended for said interface 15, comprising data relating to a determined action, which was elaborated and estimated beforehand in the step 106. Said action will have to be accomplished by the owner, the operator or more generally the user of the medium. Once the message has been decoded and rendered by said interface 15, said user can thus become aware of the recommended corrective action and carry it out himself/herself.

The evolution of a first parameter P1 of a medium can be related to the evolution of a second parameter P2 of the same medium. Thus, it can therefore be necessary to monitor the simultaneous evolution of a plurality of parameters P1 and P2 during the triggering of a corrective action, for example, by estimating the impact of a corrective action elaborated for a first parameter P1 on the nominal value P2 (t+n) of a second parameter P2. As a variant and additionally, the method 100 can then comprise a step 108 for estimating a nominal value P2 (t+n) of a second parameter P2, according to an action elaborated previously for the first parameter P1 during the step 106. As a nonlimiting example, during a variation of the value of the first parameter relating to the pH, the second parameter relating to the oxidation-reduction potential of a swimming pool can become unstable. To anticipate this instability, it can be necessary to estimate a nominal value P2 (t+n) of the parameter P2 relating to the oxidation-reduction potential with regard to the corrective action elaborated for the first parameter P1 relating to the pH. This anticipation of the effect on all or some of the parameters of the medium can make it possible to avoid triggering corrective actions that are ineffective and/or unproductive or even disruptive for the equilibrium of the medium.

Such a step 108 can moreover consist in estimating and updating the current value P2 (t) of a second parameter of the medium P2. In fact, certain current values Px (t) of parameters Px of the medium can be estimated. For example, this is the case of the value of the chlorine stabilizer known under the name of isocyanuric acid, which can in general not be measured by conventional sensing means SenM. As a nonlimiting example, a corrective action seeking to increase the value of the oxidation-reduction potential can consist in adding an estimated quantity of chlorine. Such a chemical agent is generally introduced jointly with a determined quantity of isocyanuric acid. The addition of chlorine can thus cause a variation of the current value P2 (t) of the parameter P2 related to the isocyanuric acid in a deterministic manner.

According to a second situation symbolized by the link 104-n in FIG. 3, the value of field for storing a time limit value Cx of a parameter Px can be a predetermined value which characterizes an end of a recovery period. More precisely, such a value means that the estimated waiting time period for a corrective action to produce its effects has been reached. As mentioned above, such a second situation can result from a counter value Cx of zero, or, in the case in which the time limit value Cx comprises an absolute timestamp, said time limit value is less than the current date.

The method 100 then comprises a step 112, which is identical to the above-described step 105, for estimating a distance Δ between the nominal value Px (t+n) and the current value Px (t). If said step 112 confirms a distance Δ which is substantially zero, that is to say if the current value Px (t) of the parameter Px has recovered a perceptible normality, then said method 100 comprises a step 110 for acknowledging the time limit Cx of such a corrective action. As a nonlimiting example, such a step 110 can consist in updating the recording associated with the parameter Px and registering in the field for storing a time limit value Cx the predetermined value characterizing an absence of a definition of a time limit. Possibly, the step 110 can be implemented routinely when the distance Δ is zero.

On the other hand, if said step 112 confirms a distance Δ which is not zero, that is to say if the current value Px (t) remains different or far from the nominal value Px (t+n), then said method 100 comprises a step 113 for correction of the corrective action elaborated and triggered beforehand during the step 106 and 107, respectively, said corrective action being considered not to have produced the expected effects. In order to correct such a corrective action, the step 113 can comprise a step 113a for estimating a new nominal value Px (t+n) according to one of the methods mentioned above. As a variant or additionally, said step 113 can comprise a step 113b for defining a new time limit value Cx according to one of the methods mentioned above. According to this variant, the processing unit PU grants an additional time period for the parameter to recover its normality without triggering a new corrective action. As a variant or additionally, the step 113 can comprise a step 113c consisting in elaborating a third corrective action, which is different from that elaborated and triggered in a preceding period. As a non-limiting example, such a third corrective action can consist in verifying the current value of a second parameter P2, for example, the current value P2 (t), as a non-limiting example, corresponding to the current value of the CAT. In fact, when the value of the CAT is less than eighty (80) milligrams per liter, the pH can become unstable. It is then necessary to increase the concentration of the CAT in the water of a swimming pool by the addition of a suitable chemical agent. Such a third corrective action can moreover consist in elaborating an instruction intended for a user of the system and in triggering the rendering of a said instruction by the human-machine rendering interface 15. As an example, such an instruction can consist in prompting the user to check the state of the equipment of his/her swimming pool, for example, the operational state of an automated filtration device.

As already mentioned, the processing unit PU of a regulation system according to the invention can also cooperate with a data structure associated with different corrective actions, said structure of actions comprising one or more recordings associated with one or more corrective actions, not represented in the figures for the sake of simplicity. Each recording can moreover comprise an action identifier, an identifier of a medium parameter Px, and/or an attribute characterizing an execution priority. Thus, the step 106 for elaborating a corrective action in connection with a medium parameter Px can consist in searching in said structure of actions for a recording dedicated to a high-priority corrective action characterized, for example, by a value such as the whole-number value "1" and associated with the parameter Px. During the implementation of the of step 113 for correction of a corrective action, said step 113 can consist in searching for a recording associated with a corrective action of lower priority, characterized, for example, by a higher whole-number value such as the value "2" and associated with the parameter Px. The corrective actions thus elaborated during the step 113 can be triggered during the step 107 for triggering a previously described corrective action.

As a variant or additionally, a method 100 according to the invention can comprise a step, not represented in FIG. 3 for the sake of simplicity, before the step 113 for elaborating a correction of an action, for rendering by means of the human-machine interface 15 a confirmation message intended for the user or the operator of the medium, said message being elaborated by the processing unit PU in order to verify the accomplishment of the action recommended to the user during the step 107. The step 113 for elaborating an action correction is implemented if and only if the processing unit PU decodes an acknowledgment message beforehand, which was transmitted by the human-machine interface 15, comprising an attribute characterizing an accomplishment of an action in reaction or in response to the interpretation of said confirmation message by the user.

As a variant or additionally, a method 100 according to the invention can comprise, after the step 110 for acknowledging the time limit Cx of an action relating to a parameter Px, a step 111 for estimating the nominal value P2 (t+n) and/or the current value P2 (t) of a second parameter P2 based on the corrective action acknowledged during the step 110. As a non-limiting example, the medium can have recovered an equilibrium following an addition of a disinfecting chemical agent, such as, for example, chlorine, such an addition being connected with the oxidation-reduction potential. The current value P2 (t) of a second parameter P2, for example, isocyanuric acid, must then be increased by one unit. In fact, the concentration of isocyanuric acid, consisting of a chlorine stabilizer, cannot be measured by measurement instruments. It must be estimated when a chlorine pellet is added in a skimmer, for example.

According to a third situation symbolized by the link 104-y in FIG. 3, the value of the field for storing a time limit value Cx can consist of a value other than a predetermined value characterizing an absence of a time limit definition or an end of a recovery period. Thus, the method 100 can comprise a step 109, identical to the step 105 described above, for estimating a distance $\Delta$ between the nominal value Px (t+n) and the current value Px (t) of a parameter Px. If said step 109 confirms a distance $\Delta$ which is substantially zero, that is to say if the parameter in consideration has recovered its normality more rapidly than expected, the processing unit PU can implement the step 110 for acknowledging the time limit Cx. In the opposite case, the current iteration of the method 100 is completed: the method 100 will be implemented again in the next iteration.

Thus, we can note that, in contrast to a system according to the prior art, the invention makes it possible not to immediately undertake a new corrective action in order to seek to correct the physico-chemical parameter in consideration or more generally the medium, for example, by adding an active chemical agent. Quite to the contrary, when a method according to the invention detects an "abnormal" value Px (t) of a physico-chemical parameter Px, said method grants time to time according to a well-known metaphor, so that the corrective action undertaken previously, wherein a time limit value Cx was initialized, said time limit reflecting an action time, can produce its effect. Thus, the invention makes it possible to add or introduce a minimum of corrective chemical agents, taking into consideration a time necessary for accomplishing a corrective action. To illustrate this advantage, let us use the example of a basin of a swimming pool whose coating is by nature intrinsically alkaline, that is to say, whose coating, due to its structure and/or composition, inexorably results, upon simple contact, in a pH above 7 of the water of said basin. While a corrective action seeking to add an acidic chemical agent such as hydrochloric acid or an agent referred to conventionally as a "pH-" product to a basin with a different coating has a nearly instant effect, said corrective action can require an additional time in the basin in consideration due to said alkaline coating. A known system would tend to require the addition of such an acid or directly adding such an acid continuously as long as the parameter Px, in this case the pH, has not recovered a value close to 6.9, even if this excessive and continuous addition of agent induces in turn an imbalance resulting in an addition of an agent which is now alkaline to correct an excessively low pH and so on, as in a yo-yo movement or a toy in permanent imbalance. The system and method according to the invention do not use such a supplementary addition of hydrochloric acid, but instead allow the latter to act for the necessary time determined by the time limit Cx, thus minimizing the addition of corrective chemical agents.

According to a variant or additionally, the step 102 for reading the current value Px (t) of a physico-chemical parameter Px can moreover consist in reading a preceding current value Px (t−n) and calculating a new current value from said read values. This variant can make it possible to limit an excessively high reactivity or variability of a parameter, or even to anticipate a future impact of the environment on the medium, by intentionally altering the current value of said parameter. According to an embodiment example, such a preliminary calculation can consist in calculating an average of the current value Px (t) and the current values of said parameter Px of one or more elapsed periods t−n. The step 102 then can consist in reading and extracting the respective values of said elapsed periods, and then calculating the average of said values according to known IT functions.

As a variant or additionally, the step 102 for reading the current value Px (t) of a physico-chemical parameter Px can moreover consist in seeking and reading in the data storage means DSM one or more anticipation data and calculating, according to known mathematical methods, a new current value of the parameter Px based on said read anticipation data values.

When combined with the current value Px (t), using known calculation methods, the anticipation data can make it possible to anticipate events or disturbances that can disrupt the equilibrium between parameters of a medium. The objective of such an anticipation is to trigger a corrective action, in anticipation of a future imbalance, for example, in anticipation of an increased occupancy load of a basin of a swimming pool, in order to substantially maintain or recover an equilibrium more rapidly after said disturbance. Such an action can be likened to a preventive treatment of the water of the swimming pool by anticipating such a disturbance. Such an anticipation action can thus consist in adding a disinfecting chemical agent at low concentration before the occurrence of the disturbance, in particular for preparing the medium for such a disturbance by administering a treatment with a lower quantity of chemical agent in comparison to the corrective treatment without anticipation after the occurrence of the disturbance. In the same manner, it is possible to minimize or simplify any possible automatic or manual corrective actions which are connected with such a disturbance thanks to such an anticipation. As non-limiting examples, acid rain can cause the value of the pH of a swimming pool to drop. The anticipatory addition of alkaline chemical agent at low dose, before the next occurrence of such a rain, will make it possible to attenuate and even avoid any loss of equilibrium. In the same manner, according to another example, an increase in the occupancy load of a swimming pool can cause the oxidation-reduction potential to decrease. An anticipatory addition of a relevant chemical agent will make it possible to raise the value of said oxidation-reduction potential and thus guarantee an optimal water disinfecting power when there is an increase in the occupancy load.

According to another embodiment variant of a method according to the invention, the latter can comprise a step for calculating the current value P3 (t) of a physico-chemical parameter P3 synthesized or calculated based on the measurable and/or calculatable current values of other parameters P1 and P2. Thus, the step 102 can consist in extracting respective first and second current values P1 (t) and P2 (t) of first and second recordings respectively dedicated to or associated with first and second parameters P1 and P2 of the medium and estimating a third current value P3 (t) of a third parameter P3 based on said first and second current values P1 (t) and P2 (t) and writing said third current value P3 (t) thus estimated in said third recording. Thus, the storage means DSM can comprise a recording RP3 dedicated to or associated with said third parameter P3 of the medium, corresponding, for example, to the Langelier index IS. The current value P3 (t) can thus be estimated or calculated based on the current value of the pH, the value of the dissolved solids TDS, the alkalinity of the water CAT, and the Hydrotimetric Titer HT, and the temperature T of the water. Said step 102 thus consists in reading and extracting the current values of said parameters necessary for such a calculation, and in then generating said current value according to a given treatment, for example, according to the equation: IS=pH+T+HT+CAT−TDS. Said generated value can then be registered as current value P3 (t) of said parameter P3.

As a variant or additionally, a method 100 according to the invention can moreover comprise a step, not represented in the figures, for initializing or updating the content of the storage means DSM and/or PSM. Such an initialization can consist in assigning to the nominal values Px (t+n) values originating from statistics or averages elaborated based on a data base containing data collected by sensing means SenM of several regulation systems according to the invention. Such a collection and such an intersection of values originating from a plurality of media similar to the medium in consideration make it possible to estimate general behaviors of said media. The structure associated with the corrective actions can moreover be initialized or updated periodically based on statistical values and/or actions elaborated based on a plurality of data originating from similar media. The method 100 can thus comprise a step, not represented in the figures, for exporting such data and for forming or enriching such a data base.

The invention was described primarily in connection with the maintenance of a physico-chemical parameter of a specific medium, more particularly the pH of the water of a swimming pool. As a variant or additionally, a method 100 according to the invention can be applied to any other parameter of the medium in consideration, such as, for example, the oxidation-reduction potential, the CAT, the HT, the TDS or any other measurable parameter in the medium.

In addition, the invention was described in the case of its use in connection with the management of a swimming pool. It can also be implemented for acting on any other medium such as, as an example, in the management of the equilibrium between parameters originating in the ground, in a vivarium, in an aquarium, etc.

The invention claimed is:

1. A method for maintaining an equilibrium of at least one physico-chemical parameter of a medium, said method being implemented by a processing unit of a system for regulating said medium, said processing unit cooperating with memory recording data relating to a first medium parameter, said memory comprising:

a recording dedicated to said first medium parameter and configured to store a current value of said first medium parameter and a nominal value of said first medium parameter;

said method comprises:

a step for reading the current value of said first medium parameter;

a step for reading the nominal value of said first medium parameter;

a step for estimating a distance between said nominal value and the current value;
a step for triggering an action depending on the value of said distance;
wherein:
the recording dedicated to said first medium parameter comprises a field for storing a value of a time limit date for the current value to recover to the nominal value;
said method further comprises:
before the step for triggering an action, a step for reading the value of the field for storing the time limit date;
the step for triggering the action depending on said distance being performed in response to a determination that
the value of the field for storing the time limit date comprises a predetermined value characterizing the absence of definition of the time limit date for the current value to recover to the nominal value.

2. The method according to claim 1, comprising, before the step for triggering the action, a step for elaborating said action depending on the value of said distance.

3. The method according to claim 2, wherein the step for elaborating the action comprises a step for estimating the nominal value of said first medium parameter.

4. The method according to claim 2, wherein the step for elaborating the action comprises a step for defining the time limit date for the current value to recover to the nominal value depending on said action.

5. The method according to claim 3, wherein the step for triggering the action comprises updating the recording dedicated to said first medium parameter in order to register in it the nominal value of said first medium parameter or the time limit date for the current value to recover to the nominal value depending on said action.

6. The method according to claim 1, wherein:
the processing unit cooperates with an actuator in order to implement the action;
the step for triggering the action comprises elaborating a command intended for said actuator in order to implement the action depending on the estimated distance.

7. The method according to claim 1, wherein:
the processing unit cooperates with a human-machine rendering interface;
the step for triggering the action comprises elaborating an instruction intended for a user of said system and triggering the rendering of said instruction by the human-machine rendering interface.

8. The method according to claim 2, wherein:
the memory stores a second recording dedicated to a second medium parameter and configured to store a nominal value and a current value of said second medium parameter;
said method comprises, after the step for elaborating an action, a step for estimating a nominal value and/or a current value of said second parameter depending on the previously elaborated action.

9. The method according to claim 1, comprising a step for acknowledging the time limit of an action, comprising registering in the field for storing a time limit date a predetermined value characterizing the absence of a definition of a time limit date, said step being implemented if the value of the distance between said nominal value and the current value confirms a distance which is substantially zero.

10. The method according to claim 1, comprising a step for correcting an action before the step for triggering an action, said correction step being implemented in response to a determination that:
the time limit date for the current value to recover to the nominal value has been reached; and
the value of the distance between said nominal value and the current value is not zero.

11. The method according to claim 10, wherein the step for correcting an action comprises a step for estimating a new nominal value of said first medium parameter.

12. The method according to claim 10, wherein the step for correcting an action comprises a step for defining a time limit date for the current value to recover to the nominal value depending on said correction of an action.

13. The method according to claim 1, wherein:
the memory stores a current value of a preceding period;
the step for reading the current value moreover comprises reading the preceding value and calculating a new current value based on said read values.

14. The method according to claim 1, wherein:
the memory stores anticipation data;
the step for reading the current value of the first medium parameter further comprises reading the anticipation data and calculating a new current value based on said anticipation data.

15. The method according to claim 1, wherein:
the processing unit moreover cooperates with sensing means;
said method comprises, before the step for reading the current value of said first medium parameter, a step for triggering the acquisition of said value by said sensing means and registering said value as the current value.

16. A non-transitory computer-readable medium encoded with a computer program comprising program instructions which can be executed by a processing unit of an electronic module, said processing unit cooperating with sensing means and memory, which, when they are executed or interpreted by said processing unit, trigger the implementation of a method for maintaining an equilibrium of a physicochemical parameter of a medium according to claim 1.

17. An electronic module comprising a processing unit cooperating with sensing means and memory, said electronic module comprising, in memory, instructions of a computer program according to claim 16.

* * * * *